United States Patent

Heine et al.

[11] Patent Number: 6,139,491
[45] Date of Patent: Oct. 31, 2000

[54] FIBRE-OPTIC LARYNGOSCOPE SPATULA WITH AN EXCHANGEABLE LIGHT-GUIDE PART

[75] Inventors: Helmut A. Heine, Herrsching; Dieter Fottner, Paehl; Ulrich Bauer, Puergen, all of Germany

[73] Assignee: Heine Optotechnik GmbH & Co. KG, Herrsching, Germany

[21] Appl. No.: 09/190,145

[22] Filed: Nov. 12, 1998

[30] Foreign Application Priority Data

Nov. 13, 1997 [DE] Germany ............... 297 20 146 U

[51] Int. Cl.⁷ .................................................. A61B 1/267
[52] U.S. Cl. ........................ 600/199; 600/190; 600/193; 600/196
[58] Field of Search .................................. 600/185, 190, 600/191, 193, 196, 197, 199

[56] References Cited

U.S. PATENT DOCUMENTS

| | | |
|---|---|---|
| 4,565,187 | 1/1986 | Soloway . |
| 4,570,614 | 2/1986 | Bauman . |
| 4,958,624 | 9/1990 | Stone et al. . |
| 5,443,058 | 8/1995 | Ough ........................ 600/188 |
| 5,529,570 | 6/1996 | Storz . |
| 5,800,344 | 9/1998 | Wood, Sr. et al. ............ 600/185 |
| 5,873,818 | 2/1999 | Rothfels ........................ 600/188 |

FOREIGN PATENT DOCUMENTS

| | | |
|---|---|---|
| 0 586 972 A1 | 3/1994 | European Pat. Off. . |
| 85 26 662 0 U | 9/1985 | Germany . |

*Primary Examiner*—Linda C. M. Dvorak
*Assistant Examiner*—Brad C. Blaise
*Attorney, Agent, or Firm*—Birch, Stewart, Kolasch & Birch, LLP

[57] ABSTRACT

A fibre-optic laryngoscope spatula (1) having a light-exiting first end and an opposite second end and comprising a base part (1) and an exchangeable light-guide part (8) having a first spring-loaded coupling member (14). The base part (1) and the light-guide part (8) are designed to fit precisely together in such a way that the light-guide part (1) can be pushed into the base part (1) from the second end as far as an end position and can be pushed out of the base part (1) from the end position in the opposite direction. When in the end position, the light-guide part (8) and the base part (1) are connected to one another by means of a snap connection and have interengaging surface parts which do not allow relative movement between the base part and light-guide part in any other than the push-out direction. Furthermore, when in the end position, at least one snap connection force has to be overcome in order to allow relative movement between the base part (1) and light-guide part (8) in the push-out direction.

9 Claims, 3 Drawing Sheets

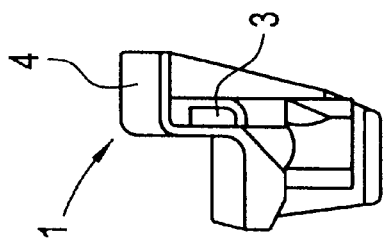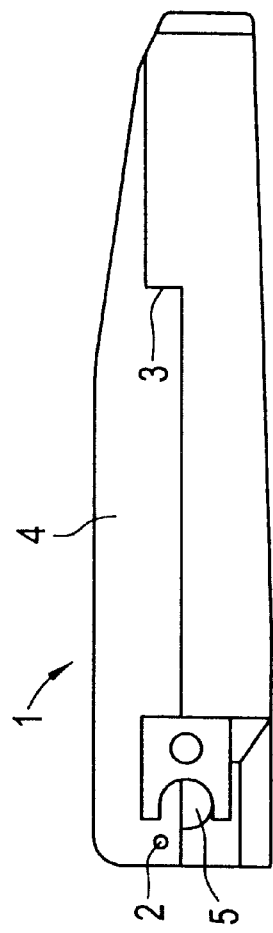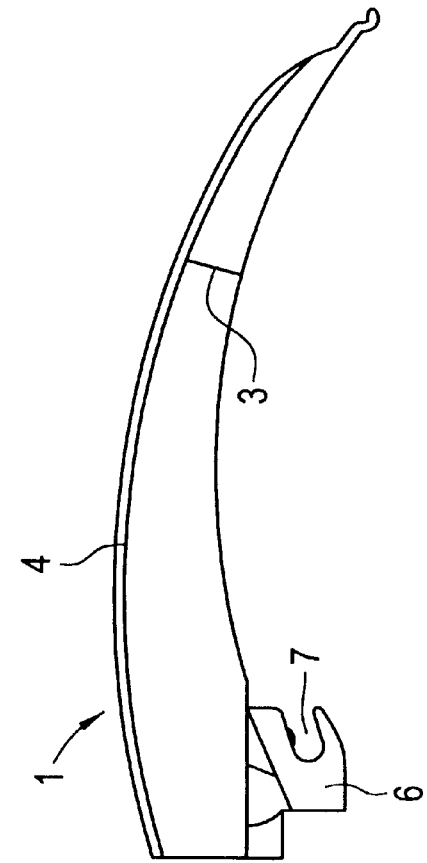

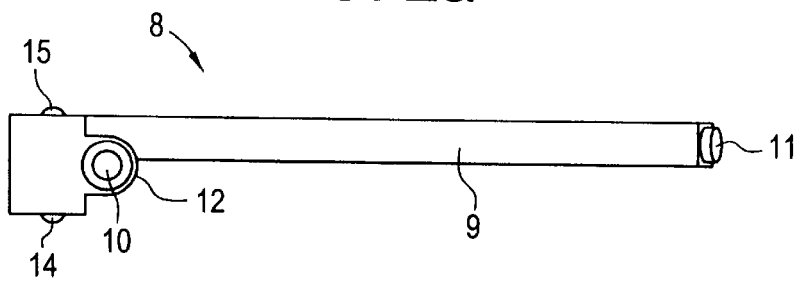
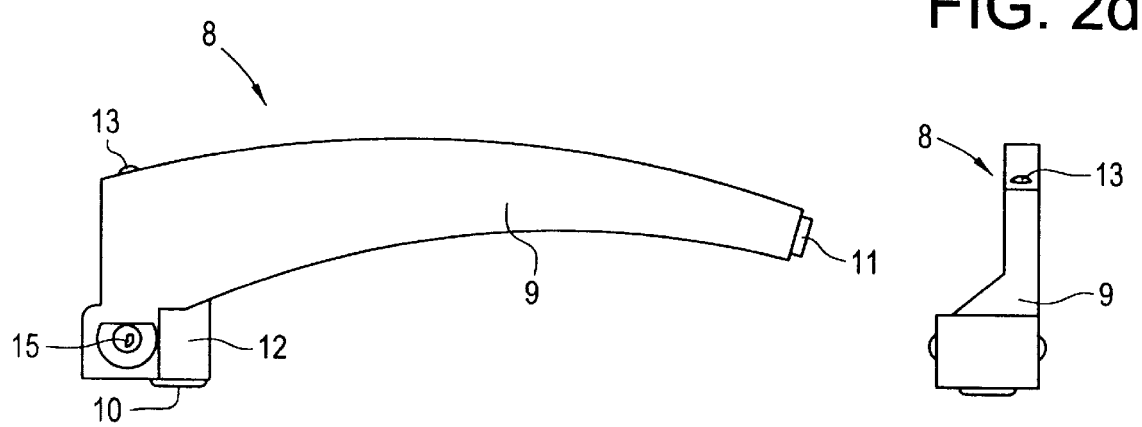
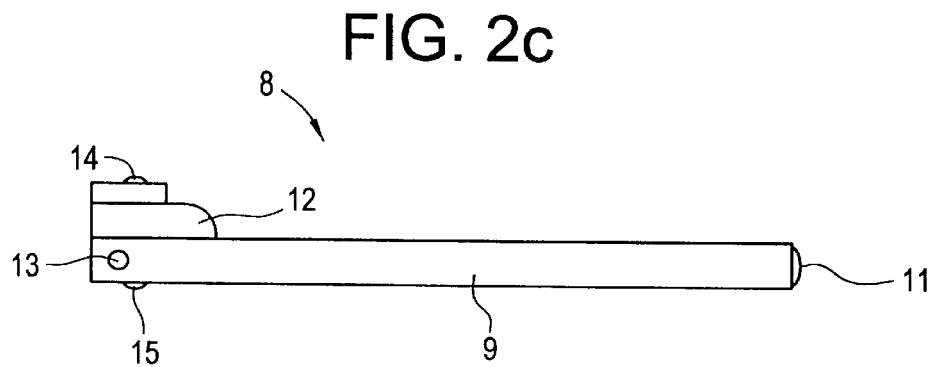

FIBRE-OPTIC LARYNGOSCOPE SPATULA WITH AN EXCHANGEABLE LIGHT-GUIDE PART

BACKGROUND OF THE INVENTION

This invention relates to a fibre-optic laryngoscope spatula having a light-exiting first end and an opposite second end and being of the kind comprising a base part and with an exchangeable light-guide part having a spring-loaded coupling member.

Light guides, while being used, undergo a natural ageing process, during which the optical properties, in particular the transparency, of the light guides deteriorate. The light guides in the fibre-optic laryngoscope spatula are subject to this ageing process to a particularly pronounced degree, since they are exposed to violent thermal shocks during cleaning and sterilization, which are necessary after every use of the fibre-optic laryngoscope spatula, and the end faces of the light guides may suffer mechanical and chemical/thermal damage. As a rule, therefore, light guides in fibre-optic laryngoscope spatulas become unusable relatively quickly and when the other components of the fibre-optic laryngoscope spatula still have good practical properties.

So that the period of practicability of the fibre-optic laryngoscope spatula as a whole is not determined by the relatively short period of practicability of the light guides contained in it, fibre-optical laryngoscope spatulas with an exchangeable light-guide part have been developed. The advantage of such spatulas is that, after the transparency of the light-guide bundle falls below a particular threshold in relatively wide wavelength ranges due to ageing, it is only necessry to replace the old light-guide part with a new light-guide part. There is no need to purchase a complete new fibre-optic laryngoscope spatula.

A fibre-optical laryngoscope spatula with an exchangeable light-guide part is disclosed in U.S. Pat. No. 4,570,614. According to U.S. Pat. No. 4,570,614, a plastics part provided with the light guide is pressed into a base part of the fibre-optic laryngoscope spatula, the base part being suitably shaped to receive this plastics part. Once the plastics part with the light guide and the base part have been pressed together, they can only be separated from one another with difficulty and with some inconvenience since a base-part recess receiving the plastic part with the light guide has a completely continuous wall with an exact fit.

Another fibre-optic laryngoscope spatula with an exchangeable light-guide part is known from EP-A-0,586,972. In this known fibre-optic laryngoscope spatula, a light-guide bundle is arranged in a light carrier designed as a removable small angular metal tube. This makes it possible to exchange the light-guide bundle for a justifiable outlay when it becomes unusable. According to EP-A-0,586,972, the removable tube with the light-guide bundle is installed by first pushing one leg into a tube or recess provided in a first region of the fibre-optic laryngoscope spatula and is then retained in position by pivoting the other leg laterally into a recess or orifice provided in a second region of the fibre-optic laryngoscope spatula.

In addition to the light guide, there is another part of a fibre-optic laryngoscope spatula which is subject to increased wear. This other part is a spring-loaded coupling member, e.g a spring-loaded coupling pin, which, when the fibre-optic laryngoscope spatula is locked into a laryngoscope handle, engages in a corresponding inner recess in the coupling region of the laryngoscope handle. This spring-loaded coupling member, which is often designed as part of a spring-loaded catch, e.g. a ball catch, may lose its tension force as a result of frequent locking and unlocking operations and as a result of thermal shocks and chemical/thermal effects caused by frequent cleaning and autoclaving operations which are necessary after every use of the fibre-optic laryngoscope spatula. It is therefore desirable to have the possibility of exchanging not only the light-guide part, but also the part of the fibre-optic laryngoscope spatula which contains the spring-loaded coupling member. This is not possible, however, either in the known fibre-optic laryngoscope spatula disclosed in U.S. Pat. No. 4,570,614 or in the known fibre-optic laryngoscope spatula disclosed EP-A-0, 586,972, where the spring-loaded coupling member is integrated into the base part of the fibre-optic laryngoscope spatula.

Another known fibre-optic laryngoscope spatula is the "Emac" type by the company Welch Allyn. This known type of fibre-optic laryngoscope has an exchangeable light-guide part which is designed in such a way that its spring-loaded coupling member or pin is seated in the exchangeable light-guide part and is always replaced simultaneously with the latter. This known Welch Allyn fibre-optic laryngoscope spatula can thus be broken down into two basic parts—the light-guide part with the spring-loaded coupling pin and the base part which has no movable components. Consequently, the base part is particularly robust and is rarely susceptible to faults. All those parts of the fibre-optic laryngoscope spatula which are subject to more rapid wear caused by ageing and which are susceptible to faults are located in the exchangeable light-guide part. Advantages therefore also arise in the area of sterilization which, if appropriate, can be carried out separately in differently controlled cycles for the two basic parts.

A disadvantage of the known Welch Allyn fibre-optic laryngoscope spatula is that the base part and the light-guide part are connected together by means of a screw, as disclosed in U.S. Pat. No. 4,958,624. The necessary opening and closing of the screw connection to exchange the light-guide part requires the use of a screwdriver which is inconvenient and laborious, especially since fibre-optic laryngoscope spatulas are used in the medical/surgical sector in which screwdrivers are not included in the tools of the trade which are constantly available. Moreover, the screw may be misplaced or lost completely due to carelessness when the light-guide part is being exchanged, with the result that time may have to be spent in looking for the screw or in procuring a replacement screw.

The object on which the invention is based is to provide a fibre-optic laryngoscope spatula with a base, part and with an exchangeable light-guide part having a spring-loaded coupling member, in which spatula the light-guide part can be exchanged in a simple way without any aids.

SUMMARY OF THE INVENTION

According to principles of the invention, a fibre-optic laryngoscope spatula has a light-exiting first end and an opposite second end and includes a base part and an exchangeable light-guide part having a first spring-loaded coupling member. The base part and the light-guide part are designed to fit precisely together in such a way that the light-guide part can be pushed into the base part from the second end as far as an end position and can be pushed out of the base part from the end position in an opposite direction. In the end position, the light-guide part and the base part are connected to one another by a snap connection and have interengaging surface parts which do not allow relative movement between the base part and light-guide part in any other than the push-out direction, and at least one snap connection force has to be overcome in order to allow relative movement between the base part and light-guide part in the push-out direction.

There are additional advantageous and preferred embodiments of a fibre-optic laryngoscope spatula according to the invention.

In one such embodiment, in the end position the light-guide part is mounted particularly reliably and firmly in the base part, since the engagement of the light-exiting end of the light-guide part in the light-exiting orifice of the base part provides additional mounting.

BRIEF DESCRIPTION OF THE DRAWINGS

Embodiments of the invention will now be described, by way of example only, with particular reference to the accompanying drawings, which are not necessarily to scale being intended to mainly to illustrate the invention, in which:

FIG. 1a is a top view from a handle side of a base part of a fibre-optical laryngoscope spatula according to the invention;

FIG. 1b is a side view of the base part shown in FIG. 1a;

FIG. 1c is a view from a push-in side of the base part shown in FIG. 1a;

FIG. 2a is a top view from the handle-side of a light-guide part of the fibre-optic laryngoscope spatula according to the invention;

FIG. 2b is a side view of the light-guide part shown in FIG. 2a;

FIG. 2c is a top view of the light-guide part shown in FIG. 2a but viewed in the opposite direction to the view of FIG. 2a;

FIG. 2d is a view of the light-guide part shown in FIG. 2a viewed in the push-in direction;

FIG. 3b is a view in the push-in direction of the assembled spatula shown in FIG. 3a; and FIG. 3c is a view from the other side of the assembled spatula shown in FIG. 3a.

DESCRIPTION OF THE PREFERRED EMBODIMENTS

Figure 3A:
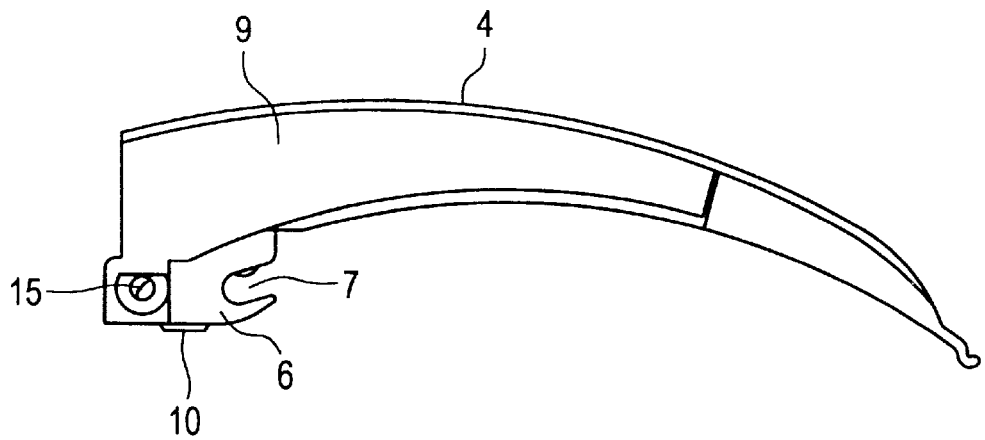
FIG. 3a is a view of the base part of FIG. 1a and the light-guide part of FIG. 2a when assembled together to provide the assembled fibre-optic laryngoscope spatula according to the invention, the view being a side view from the side of the light-guide part.

The basic design of a base part 1 of a fibre-optic laryngoscope spatula according to the invention is similar to that of a conventional Macintosh spatula, as illustrated in FIGS. 1a to 1c. The base part 1 has a top member 4 and a coupling part 6. By providing a first cutout 7 in the coupling part 6, the base part 1 can be suspended in a laryngoscope handle in a way known from the prior art. In addition to the first cutout 7, the base part 1 has a second cutout 5 which is orthogonal to the first cutout 7 and which serves to receive a portion of an associated light-guide part 8 in an exact or precise fit (see FIGS. 2a to 2d).

On its light-exiting side, the member 4 terminates in a bead having an orifice 3 which serves to receive a light-exiting end of the light-guide part 8. Furthermore, the member 4 has, near that end of the base part 1 located opposite the orifice 3, a small recess 2 whose function is explained further below.

The base part 1 is not provided with light guides or any movable parts.

Figure 3B:
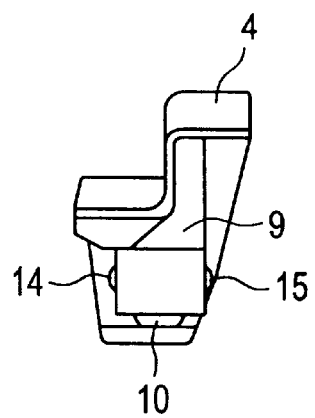
Figure 3C:
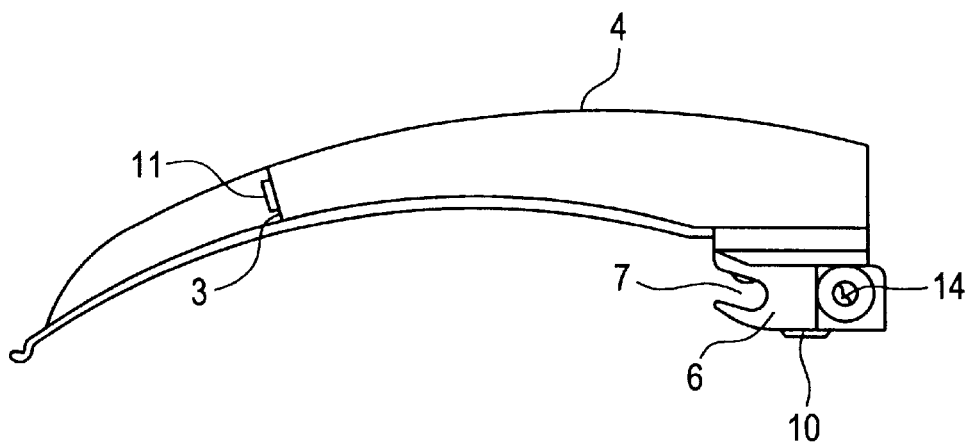

The light-guide part 8 of the embodiment of the fibre-optic laryngoscope spatula according to the invention has a basic body 9 conveniently made of autoclave-resistant plastics material and through which a light-guide bundle is led from a light-entry orifice 10 to a light-exiting orifice 11 (see FIGS. 2a to 2d). The base part 1 and the light-guide part 8 are designed to have an exact fit in such a way that the light-guide part 8 can be pushed or inserted into the base part 1, below the member 4, from that end of the fibre-optic laryngoscope spatula located opposite the light-exiting end as far as an end position and can be pushed out of the base part 1 from the end position in the opposite direction. In the described embodiment of the fibre-optic laryngoscope spatula according to the invention, the end position is obtained when a bead-like pedestal portion 12 of the light-guide part 8 abuts against a wall of the second cutout 5 in the coupling part 6 of the base part 1. A spring-loaded coupling member, e.g. a pin 13, which is referred to below as a "second spring-loaded coupling pin", simultaneously locks into the recess 2 of the member 4, so that a snap connection is made. In the end position, the light-exiting end of the light-guide part 8 engages in, and projects slightly beyond, the orifice 3 of the base part 1. FIGS. 3a to 3c show the described embodiment of the fibre-optic laryngoscope spatula according to the invention with the parts assembled in the end position.

As is evident from FIGS. 3a to 3c, the base part 1 and light-guide part 8 are shaped to have a precise or exact matching fit when in the end position. In particular, when the parts 1 and 8 are assembled in the end position, relative movement between the base part 1 and light-guide part 8 is not possible in any other than the push-out direction. If the light-guide part 8 is to be disengaged from the base part 1 by pushing the base part 1 from the end position, the force of the snap connection, consisting of the second spring-loaded coupling pin 13 received in the recess 2 in the member 4, must be overcome. The spatula is designed for such disengagement to be possible with a justifiable effort merely by using the force of a thumb without any aids. So that the force required for this purpose is kept within suitable limits, the pin 13 conveniently has a rounded end or may be in the form of a "ball" so that the snap connection is a spring-loaded catch or ball catch.

In addition to having the second spring-loaded coupling pin 13, the light-guide part 8 also has, in its pedestal region 12, a first spring-loaded coupling member, e.g. pin 14, and a third spring-loaded coupling member, e.g. pin 15. These spring-loaded coupling pins 14 and 15 are arranged mirror-symmetrically relative to one another and, in each case, orthogonally to the second spring-loaded coupling pin 13. As with pin 13, the "pins" 14 and 15 suitably have rounded ends or may even be in the form of "balls" and form part of a spring-loaded catch or ball catch. After the base part 1 and light-guide part 8 have been assembled in the end position, the fibre-optic laryngoscope spatula described can be suspended in the laryngoscope handle by means of the first cutout 7 in the base part 1 and thereafter, as is known from the prior art, can be swung up and locked into the laryngoscope handle with the aid of the first and third spring-loaded coupling pins 14 and 15.

The invention claimed is:

1. A fibre-optic laryngoscope spatula having a light-exiting first end and an opposite second end and comprising a base part and an exchangeable light-guide part having a first spring-loaded coupling member for engaging the laryngoscope spatula with a laryngoscope handle on which the laryngoscope spatula is to be mounted, said fibre-optic laryngoscope spatula also including a snap connector coupling member for interconnecting the base part and the light-guide part wherein the base part and the light-guide part have further inter-engaging surface parts which are structured to fit precisely together in such a way that a light-entry second end of the light-guide part can be pushed into a light-exiting first end of the base part in a push-in direction as far as an end position in which the light-guide part and the base part are interconnected to one another by the snap connector coupling member, said inter-engaging surface parts being structured such that they do not allow substantial relative movement between the base part and light-guide part in any direction other than a push-out direction, which is opposite to said push-in direction and wherein at least a snap connection force of the snap-connector coupling member has to be overcome in order to allow relative movement between the base part and light-guide part in the push-out direction.

2. The fibre-optic laryngoscope spatula according to claim 1, wherein the snap-connector coupling member is a second spring-loaded coupling member and is arranged in the light-guide part, above the light-entry second end thereof, in such a way that, in the end position, the second spring-loaded coupling member engages in a base-part recess and, with the recess, forms said snap connection force.

3. The fibre-optic laryngoscope spatula according to claim 1, wherein the light-guide part has a basic body made of autoclave-resistant plastics material.

4. The fibre-optical laryngoscope spatula according to claim 1, wherein the base part has, at its light-exiting first-end, an orifice, in which a light-exiting first-end of the light-guide part engages in said end position.

5. The fibre-optic laryngoscope spatula according to claim 1, wherein the first spring-loaded coupling member comprises part of a ball catch.

6. The fibre-optic laryngoscope spatula according to claim 1, wherein the snap connector coupling is a second spring-loaded coupling member which is structured as a ball catch device.

7. The fibre-optic laryngoscope spatula according to claim 1, in which a third spring-loaded coupling member is located mirror-symmetrically opposite said first spring-loaded coupling member.

8. The fibre-optic laryngoscope spatula according to claim 7, wherein said third spring-loaded coupling member is structured as part of a ball catch.

9. The fibre-optic laryngoscope spatula according to claim 1, in which each of the first spring-loaded coupling member and the snap connector coupling memeber comprises a spring-loaded coupling pin.

* * * * *